(12) United States Patent
Taro

(10) Patent No.: US 11,457,842 B2
(45) Date of Patent: Oct. 4, 2022

(54) METHOD AND APPARATUS FOR DETERMINING A DETERIORATION OF RESPIRATORY FUNCTION

(75) Inventor: Nicholas L. Taro, Denver, CO (US)

(73) Assignee: PATIENT SHIELD CONCEPTS, LLC, Denver, CO (US)

( * ) Notice: Subject to any disclaimer, the term of this patent is extended or adjusted under 35 U.S.C. 154(b) by 885 days.

(21) Appl. No.: 12/354,352

(22) Filed: Jan. 15, 2009

(65) Prior Publication Data

US 2009/0182210 A1  Jul. 16, 2009

Related U.S. Application Data

(60) Provisional application No. 61/021,094, filed on Jan. 15, 2008.

(51) Int. Cl.
| | |
|---|---|
| *A61B 5/145* | (2006.01) |
| *A61B 5/1459* | (2006.01) |
| *A61B 5/00* | (2006.01) |
| *A61B 5/083* | (2006.01) |

(52) U.S. Cl.
CPC ........ *A61B 5/14542* (2013.01); *A61B 5/0836* (2013.01); *A61B 5/1459* (2013.01); *A61B 5/14539* (2013.01); *A61B 5/412* (2013.01)

(58) Field of Classification Search
None
See application file for complete search history.

(56) References Cited

U.S. PATENT DOCUMENTS

| | | | |
|---|---|---|---|
| 3,043,303 A | 7/1962 | Still | |
| 3,874,850 A | 4/1975 | Sorensen et al. | |
| 3,910,256 A | 10/1975 | Clark et al. | |
| 4,109,505 A | 8/1978 | Clark et al. | |
| 4,535,786 A | 8/1985 | Kater | |
| 4,682,895 A | 7/1987 | Costello | |
| 4,840,179 A | 6/1989 | Ullrich | |
| 5,234,835 A * | 8/1993 | Nestor et al. | 436/11 |
| 5,335,305 A * | 8/1994 | Kosa | G01N 21/7703 156/154 |
| 5,357,953 A * | 10/1994 | Merrick | A61B 5/1459 356/39 |
| 5,397,411 A | 3/1995 | Costello et al. | |
| 5,408,999 A | 4/1995 | Singh et al. | |
| 5,526,809 A | 6/1996 | Giddian-Green | |
| 5,544,651 A | 8/1996 | Wilk | |
| 5,687,718 A | 11/1997 | Fischer et al. | |
| 5,957,885 A | 9/1999 | Bollish et al. | |
| 6,053,887 A | 4/2000 | Levitas et al. | |
| 6,616,614 B2 | 9/2003 | Webber et al. | |
| 6,766,188 B2 * | 7/2004 | Soller | 600/477 |
| 6,819,951 B2 | 11/2004 | Patel et al. | |
| 6,981,947 B2 | 1/2006 | Melker | |
| 6,985,762 B2 | 1/2006 | Brashears et al. | |
| 6,986,347 B2 * | 1/2006 | Hickle | A61M 16/0093 128/200.24 |
| 7,229,430 B2 | 6/2007 | Hickle et al. | |
| 7,308,894 B2 | 12/2007 | Hickle | |
| 7,351,203 B2 | 4/2008 | Jelliffe et al. | |
| 7,398,115 B2 | 7/2008 | Lynn | |
| 2004/0059211 A1 | 3/2004 | Patel et al. | |
| 2004/0170154 A1 | 9/2004 | Carter et al. | |
| 2006/0020179 A1 | 1/2006 | Anderson et al. | |
| 2007/0049812 A1 | 3/2007 | Aoyagi et al. | |
| 2008/0194933 A1 * | 8/2008 | Kunze | A61B 5/1459 600/339 |
| 2008/0208019 A1 | 8/2008 | Nitzan | |

FOREIGN PATENT DOCUMENTS

WO  WO 1998/006726  7/1988

OTHER PUBLICATIONS

Lewanowitsch et al (Life Sciences, 2006. vol. 78. pp. 682-688).*
Baldini et al (Proc. SPIE 6585, May 31, 2007, pp. 1-7). (Year: 2007).*
Sury and Cole (Anaesthesia, 1988, vol. 43, pp. 285-288) (Year: 1988).*
Ignatov (Biosensor & Bioelectronics, 2001, vol. 16, pp. 109-113). (Year: 2001).*
International Preliminary Report on Patentability dated Feb. 20, 2009 for corresponding Application No. PCT/US2009/031148.

(Continued)

*Primary Examiner* — Celine X Qian
(74) *Attorney, Agent, or Firm* — Holzer Patel Drennan

(57) ABSTRACT

In accordance with one embodiment of the invention, a system is provided for the monitoring of blood analytes using optical probes in the circulatory system. The probes can be inserted on the venous side of the circulatory system. In another embodiment, methods and apparatuses can be used for processing continuous information generated from indwelling intravascular or tissue optical sensors including, but not limited to, measuring gas concentrations, pH, temperature, and other analytes of blood or tissue. In another embodiment, analyte values can be displayed and analyzed to determine if the values fall outside of normal physiological parameters. Trends of one or multiple analyte values can be analyzed and extrapolated to predict any impending, deleterious condition. In one embodiment, an alarm can be transmitted to appropriate personnel when criterion/criteria are met. In yet another embodiment, devices can be inhibited from delivering continuous infusions of medicine to patients.

16 Claims, 9 Drawing Sheets

(56) References Cited

OTHER PUBLICATIONS

Nitzan M. et al., "Measurement of Oxygen Saturation in Venous Blood by Dynamic Near Infrared Spectroscopy", Biomedical Optics, Apr. 2000, vol. 5, No. 5, pp. 155-162.
European Searching Authority, European Search Report, EP09701619.0, dated Jan. 7, 2014, 8 pages.
Phillips Medical Systems North America Corporation, 2002, "Point of Care Diagnostics, Champion's Gude to Neotrend L, Trendcare Continuous Blood Gas Monitoring System" pamphlet, www.medical.philips.com/pocd, 5990-0324EN, Jan. 31, 2002, 96 pages.

* cited by examiner

METHOD AND APPARATUS FOR DETERMINING A DETERIORATION OF RESPIRATORY FUNCTION

CROSS-REFERENCES TO RELATED APPLICATIONS

This application claims the benefit of U.S. provisional application 61/021,094 filed on Jan. 15, 2008 entitled "Measurement of Carbon Dioxide Using Optical Probes in Peripheral Venous System" the content of which is hereby incorporated by reference in its entirety and for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND

In the last decade, there has been a significant increase of hypoxic brain injuries and deaths in hospitalized patients who have received intravenous opioids, commonly referred to as narcotics, for pain control after surgery, a phenomenon entitled postoperative opioid-induced respiratory depression. Narcotics diminish the brain's sensitivity to carbon dioxide ($CO_2$). The normal physiological response to rising levels of $CO_2$ is hyperventilation, the body's method to exhale excess carbon dioxide. Paradoxically, in the presence of narcotics, the brain signals the respiratory system to breath less frequently than during normal respiration—a dangerous situation. As $CO_2$ in the blood rapidly increases, respiratory depression and apnea, the cessation of breathing, follow with resultant brain injury or death. Patients receiving intravenous narcotics in a hospital setting are at a higher risk of respiratory depression as opposed to those who have surgery in an outpatient ambulatory surgicenter. Outpatients are at decreased risk for respiratory depression because they typically have less invasive surgeries and receive weaker, therefore less dangerous, oral narcotics for pain relief. Per standard protocol, hospitalized patients receive powerful intravenous narcotics for pain suppression immediately following surgery. At highest risk for postoperative opioid-induced respiratory depression are geriatric, debilitated and/or obese patient populations, all of who are susceptible even to routine administration of intravenous narcotics. Similarly, patients who suffer from sleep apnea, 85% of who have not been diagnosed, or individuals habituated to narcotics, are also likely to experience depression of breathing. Furthermore, the patient population is growing older, and as a corollary, increasingly debilitated—another risk factor for respiratory depression. In the United States alone, the number of hospitalized patients at-risk for postoperative opioid-induced respiratory depression is on the order of several million per year.

It is well established moment-to-moment, that both oxygen and carbon dioxide, so called blood analytes, are critical values in the immediate health and well being of an individual. One non-invasive modality, pulse oximetry, a technology measuring the percent of hemoglobin saturated with oxygen, is routinely utilized in hospital and outpatient settings to monitor oxygenation as an ongoing reflection of respiratory status.

Unfortunately, it has been repeatedly demonstrated that when a patient is experiencing diminution of his respiratory status, monitoring with continuous pulse oximetry often gives insufficient warning to medical personnel to intervene in a timely fashion to prevent injury or death. As a result, there has been an epidemic of anoxic brain injuries and deaths from respiratory depression and/or arrest of monitored patients in hospitals. By the time the hospital staff is alerted, the patient, in many instances, is already in a dangerous condition.

A conference of 100 physician and scientists convened in 2006 to study postoperative opioid-induced respiratory depression found no medical devices currently available to adequately address the problem. Despite national recognition of this issue, it has yet to be sufficiently satisfied. Numerous technologies have attempted to monitor carbon dioxide; a gas, which builds up precipitously in the blood stream—and, consequently, the brain—when breathing is compromised and the measurement of this analyte is considered the gold standard for assessing ventilation. Most of the modalities employed for bedside monitoring of carbon dioxide are non-invasive and measure the end tidal carbon dioxide at the nose or mouth. These have been proven to be insufficient primarily because they don't assess the volume or quality of breathing. For example, they only measure the number of exhalations, i.e. breathing rate, rather than the volume of carbon dioxide actually being exhaled.

Another modality currently in clinical trials, an adhesive acoustic sensor placed over the larynx, extracts respiratory physiologic data from ambient sound vibrations occurring at the skin's surface, to calculate the respiratory rate. Again, the depth or quality of each breath cannot be evaluated. Numerous studies attempting to use apnea monitors, an alarm triggered by breathlessness, have been inadequate. One of the serious downfalls of these various trials has been the high number of false positive alarms. Studies incorporating simultaneous use of two or more of these modalities have not been entirely successful either.

As noted, one of the serious historical problems was the high number of alarms, particularly false positives. Life safety personnel must respond to false alarms before being able to determine that the alarm is actually a false one. This takes life safety personnel away from their other duties and creates less confidence among staff in the monitoring equipment. As a result, some manufacturers have provided selectable delays (for pulse oximeters, for example) so as to reduce the number of false alarms. However, this necessarily produces a further delay in responding to true alarms. Namely, a pulse oximeter that has been configured to delay the signaling of an alarm or even to inhibit the signaling of an alarm so as to avoid a false positive alarm will necessarily delay the signaling of a true alarm and thus increase the time period before life safety personnel can respond to the patient's condition.

Response time is critical in being able to maintain a patient in stable condition. For example, human physiologic stability is maintained by complex and interactive physiologic systems. This includes the interactive nature of the human respiratory system and cardiac system. When a respiratory arrest occurs, the body is deprived of additional oxygen intake. Eventually, unless respiration is restored, the patient will suffer a cardiac arrest. It is much more difficult to revive a patient that has suffered a dual arrest (i.e., both respiratory and cardiac arrest) than it is to revive a patient that has suffered only respiratory arrest. Thus, it is quite clear that the ability to respond to a respiratory arrest as quickly as possible is of benefit to the patient. Moreover, one can appreciate that given the highly interactive nature of physiological systems that in many instances a mere deterioration in respiration can result in damage to physiological systems and tissue.

SUMMARY

In accordance with one embodiment of the invention, a system is provided for the monitoring of blood analytes using optical probes in the circulatory system. In accordance with one embodiment, the probes can be inserted on the venous side of the circulatory system.

In accordance with another embodiment, a method is provided for monitoring at least one blood analyte for use in determining a deterioration of respiratory function. The method comprises obtaining a venous blood analyte measurement of a patient and determining a deterioration of respiratory function based upon the venous blood analyte measurement.

In accordance with another embodiment, a method of monitoring at least one blood analyte for use in determining a deterioration of respiratory function comprises inserting an optical probe into a tissue bed of a patient; obtaining a blood analyte measurement from said tissue bed; and determining a deterioration of respiratory function based upon said blood analyte measurement.

In accordance with another embodiment, an apparatus comprises a sensor for sensing a venous blood analyte measurement of a patient and a processor programmed to determine a deterioration of respiratory function based upon said venous blood analyte measurement.

In accordance with another embodiment, an apparatus comprises an optical probe for insertion into a tissue bed of a patient; wherein said optical probe is configured for sensing a blood analyte measurement from said tissue bed; and a processor configured for determining a deterioration of respiratory function of said patient based upon said blood analyte measurement.

In accordance with another embodiment, methods and apparatuses can be used for processing continuous information generated from in-dwelling intravascular or tissue optical sensors including, but not limited to, measuring gas concentrations, pH, temperature, and other analytes of blood or tissue.

In accordance with another embodiment, analyte values can be displayed and analyzed to determine if the values fall outside of normal physiological parameters. Trends of one or multiple analyte values can be analyzed and extrapolated to predict any impending, deleterious condition.

Further embodiments of the invention will be apparent from the specification.

DETAILED DESCRIPTION

Figure 1:
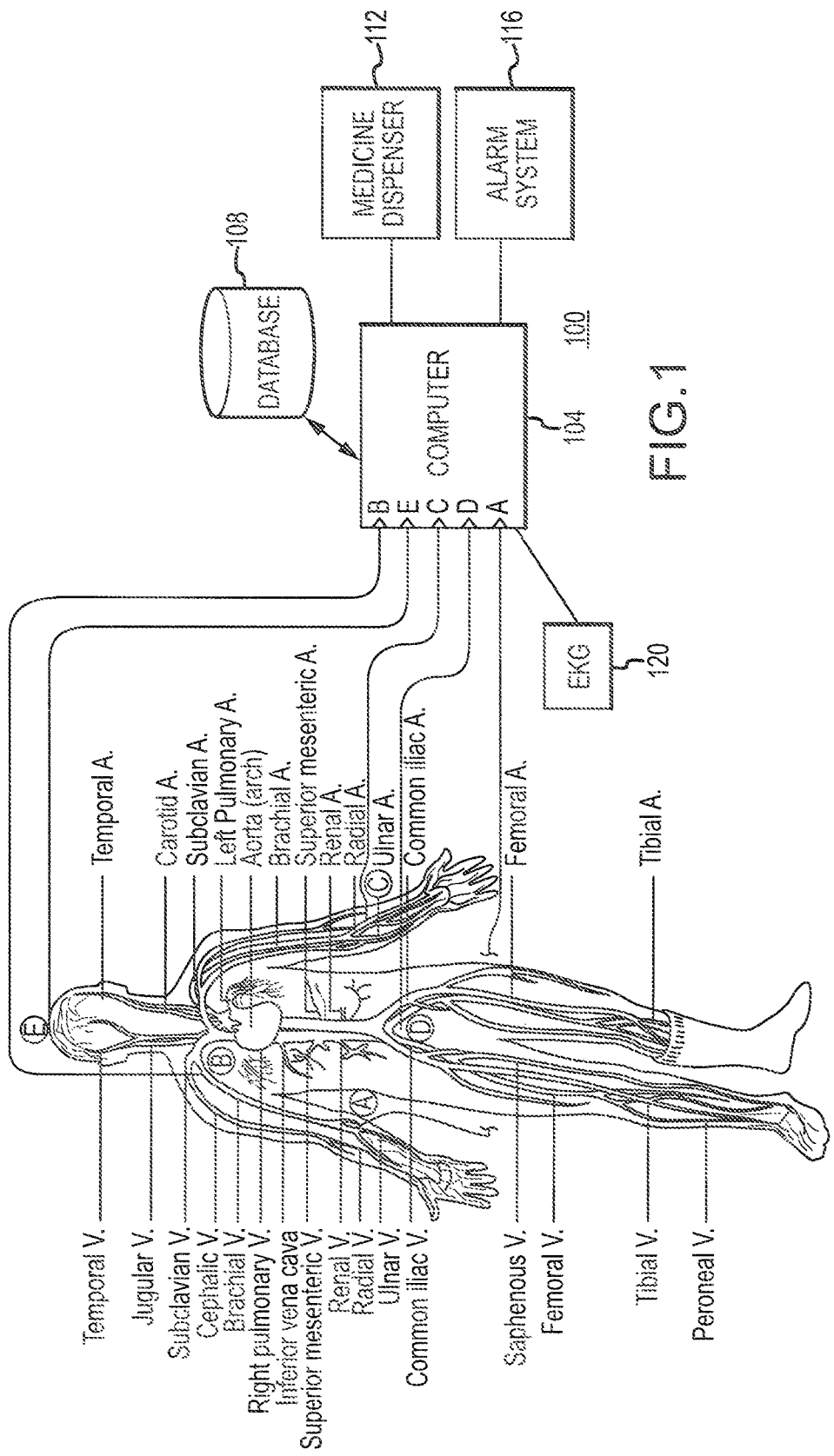
FIG. 1 illustrates a perspective view of a patient being monitored with blood analyte optical probes, in accordance with one embodiment of the invention.

As noted above, pulse oximetry is one method commonly used to monitor a patient's respiratory condition. However, pulse oximetry can be slow to detect a change in a patient's respiratory condition. It does not measure the critical ventilatory value $CO_2$ in the patient's blood. Such a delayed detection can quickly result in a deleterious respiratory condition for the patient. This is particularly true for patients in a surgical setting; but, it also applies to patients in a non-surgical setting.

In accordance with one embodiment of the invention, the monitoring of a blood analyte can be used to readily detect a change in a patient's respiratory condition. Such blood analytes can include: (1) the partial pressure of oxygen in the patient's blood (oftentimes designated as $pO_2$), (2) the partial pressure of carbon dioxide in the patient's blood (oftentimes designated as $pCO_2$), (3) the acid/base value of the patient's blood (oftentimes designated as pH), and/or (4) the temperature of the patient's blood, (5) lactic acid of the patient's blood, as well as other blood analytes.

The detection of the partial pressure of a gas in the patient's blood is quite different from pulse oximetry. Pulse oximetry is a non-invasive technique that measures the percent of hemoglobin saturated with oxygen (oftentimes referred to as the pulse oximeter oxygen saturation and designated as $S_pO_2$) in the patient's blood. In contrast, the measurement of the partial pressures of both blood gases (such as $pO_2$ and $pCO_2$) is a more accurate indicator of he patient's current respiratory status when compared to $S_pO_2$.

Similarly, current techniques for monitoring the amount of $CO_2$ in a patient's blood have significant drawbacks. Numerous technologies have been used in attempts to monitor carbon dioxide. Most of the modalities employed for bedside monitoring of carbon dioxide are non-invasive and measure the end tidal carbon dioxide at the nose or mouth. These have been proven to be insufficient primarily because they don't assess the volume or quality of breathing. For example, they only measure the number of exhalations, i.e. breathing rate, rather than the volume of carbon dioxide actually being exhaled. In contrast, measuring the partial pressure of $CO_2$ ($pCO_2$) provides an accurate reflection of blood $CO_2$ levels.

Optical Probes

In accordance with one embodiment of the invention, LED powered optical probes, or an equivalent light source, can be used to monitor blood analytes for the early detection of deleterious blood conditions. For exemplary purposes, this embodiment of the invention will be described with reference to the buildup of carbon dioxide in the blood and the damaging effect that carbon dioxide can have on the human body. However, it should be noted that in accordance with some embodiments of the invention that other conditions could be detected.

Historically, in biomedicine, the use of invasive optical sensors (or optode systems) for the detection and monitoring of physical and chemical parameters inside an animal or human date back to the 1960's. Many of these optical systems use one or multiple optical fibers for the continuous measurement of intravascular or tissue bed parameters, so called analytes, including but not limited to pH, temperature, and partial pressures of oxygen and carbon dioxide.

In the past, use of such optical sensors has not met with sustained commercial success. One explanation is that the optical systems required the use of expensive optical components to select light of specific wavelengths from a broad spectrum source. The cost of such a light source did not permit optical sensors to be readily used in a healthcare setting. Another aspect was the large size of the base unit, which housed the bulky light source, electronics, and microprocessor. As a result, use of such optical sensors has subsided and to this day it has been passed over for more user-friendly technologies.

One type of sensor that has been used in the past is the optical probe. Optical probes are miniature devices that can be inserted via a catheter into an artery in order to measure blood analytes. As noted, such optical probes have required the use of expensive optical components to serve as the light source. This increased the cost of the optical probe system and also made it bulkier and difficult to operate. In accordance with one embodiment of the invention, the former light source can now be replaced, e.g. with an LED. The LED serves as a convenient, effective, compact and inexpensive light source. Furthermore, it allows the optical probe to now be used in a vastly greater number of settings, including the use by paramedics in the field and in ambulances.

Venous Side Measurement

The preferred standard of objectively measuring ventilation has historically been the monitoring of carbon dioxide in the blood stream on the arterial side of the circulatory system. As breathing diminishes, the pressure of carbon dioxide ($pCO_2$) in the blood rises. The $CO_2$ is immediately converted into carbonic acid, a portion of which is buffered. As a consequence once the buffers are exhausted, the pH in the blood essentially falls in lock-step fashion with the rise in carbon dioxide, although there are other lesser contributors to acidemia, e.g., lactic acid from anaerobic tissue metabolism. Thus, in the setting of an acute respiratory event, measurement of pH in the blood is an indirect reflection of ventilation.

Measurement on the arterial side of the circulatory system has been preferred in the past because the pressure of oxygen in the blood, (pO2), was preferentially assessed before delivery and extraction by the tissues as occurs on the venous side, and is therefore an easily interpreted measure of lung function. For a multitude of reasons, venous pO2 is subject to much greater variation and therefore not as valuable as a single measurement.

As a result of this preference for taking measurements on the arterial side of the circulatory system, the overwhelming majority of optical sensors in human and animal studies were inserted in arteries in order to collect data for those studies. Besides being painful, insertion of a probe into an artery requires a highly skilled operator, generally a physician, to perform the task. Also, a puncture in artery, the high-pressure side of the vascular system, often resulted in significant hematoma formation or significant hemorrhage in the case of unrecognized dislodgement.

A minority of the intravascular optode system studies examined data from the central venous circulation. Access to the central venous circulatory system requires the skills of a physician specifically trained in this practice and moreover, is dangerous, even potentially fatal.

Rare studies have examined information generated from an indwelling optode system in the peripheral venous circulatory system. Such uses have been research purely oriented, rather than for treatment. Thus, none has been for the sole purpose of recognizing the critical buildup of carbon dioxide and triggering the necessary remedial action.

In accordance with another embodiment of the invention, the use of the venous system is actually encouraged rather than avoided. In fact, in accordance with one embodiment, one can utilize venous monitoring without utilizing arterial side monitoring.

Probe Insertion and Positioning

Peripheral veins are generally quite accessible and placement of an intravenous catheter is relatively easy. By mandate, virtually all patients residing in a hospital will have an indwelling intravenous catheter, usually peripheral in position, at all times. The size of an optical probe, generally less than 100 microns, allows easy insertion into the peripheral venous system through a small catheter to monitor blood analytes in accordance with this embodiment of the invention. Optical sensor studies of peripheral venous blood have yielded a strong concordance of pCO2 and pH values with simultaneously drawn central venous and arterial blood analyzed by conventional means. Thus, the insertion can place the probe in the peripheral system where blood analytes are measured.

Furthermore, it is noted that since patients often will have a peripheral venous system IV, that the insertion of an optical probe via such an IV may not necessitate a further invasive procedure on the patient. Rather, the existing IV, via a sideport device, can be used for insertion of the optical probe. In addition, the peripheral IV can be used to insert optical probes into the central venous system by routing an optical probe through the peripheral system to where it joins the central venous system. Thus, one can advance the optical probe all the way to the central venous position without having to perform an invasive and potentially dangerous procedure directly into the central venous system. Nevertheless, in some instances, one might choose to use a central venous catheter for inserting a probe.

Thus, a variety of options are available for positioning a probe. Namely, one could utilize peripheral venous insertion and take measurements from a peripheral venous location. Or, one could utilize a peripheral venous insertion and take measurements from a central venous position. Or, one could utilize a central venous insertion and take measurements from a central venous position.

In accordance with another embodiment, one could take measurements from a tissue bed. Thus, one could insert a probe subcutaneously into an organ (such as the brain), a muscle (such as the patient's deltoid muscle), or interstitial fluid (i.e., fluid that bathes a cell). Such tissue beds can provide blood analyte values that can reflect the respiratory status of the patient. Thus, they may provide a more useful position for obtaining blood analyte values under given conditions.

Monitoring

While others have attempted to rely purely on pulse oximetry to monitor respiratory status, there is clearly a need for an earlier detection system. Thus, in accordance with another embodiment of the invention, multiple continuous blood analyte values can be measured, compared, and interpreted. This will allow a system to have a higher degree of sensitivity. Furthermore, more exacting criteria may be used for alarm conditions. Thus, the number of false positive alarms can be decreased—resulting in a greater confidence in the alarm condition by healthcare personnel.

The ability to analyze continuous measurement of appropriate blood analyte values, particularly carbon dioxide and pH can be invaluable in the determination of a patient's respiratory status. It facilitates early detection of respiratory and/or cardiac deterioration, allows for earlier signaling of an alarm to appropriate medical personnel for life-saving intervention, and allows immediate inhibition of any medicine infusions or devices connected to the patient deemed to be deleterious. In addition to inhibition of a medicine, it can also provide for the administration of a substance to increase respiration.

This embodiment can utilize continuous data generated from an intravascular optical fiber or optode system, not only from arterial and central venous locations, but also preferably from the more easily accessible peripheral venous system. This information serves as input to a computer, such as a microprocessor-based device. Another embodiment may utilize additional sources of continuous medical information from other devices for integration and analysis, such as, but not limited to, an electrocardiogram, pulse oximetry and temperature.

The measurement of lactic acid is one example of how continuous data can be processed to determine the deterioration of a patient's homeostasis. Namely, a probe to measure lactic acid may be inserted into the patient's circulatory system. The probe may continuously take lactic acid measurements for use in determining if the build-up of lactic acid is occurring. In accordance with pre-determined criteria that indicate that an increase in anerobic metabolism is occurring, a computer could signal an alarm to life safety personnel and also take proactive measures to reevaluate the patient's status.

Numerous studies confirm that measurements of pH and carbon dioxide from a peripheral vein closely approximate simultaneous values taken from arterial and central venous circulations; therefore continuously measuring peripheral venous blood analytes can reflect the current respiratory status and health of the patient. This has apparently not been appreciated in the prior art nor has statistical analysis of these real-time and historical values and trends been used to detect deleterious trends, particularly those of impending respiratory failure and, but not limited to, heart failure, sepsis, ARDS, etc. and/or other organ systems as well.

In accordance with another embodiment of the invention, when this information, real or derived, falls outside of established safe ranges, and/or extrapolation of trends suggest or verify deleterious trends, an alarm condition can be triggered. The alarm can be immediately transmitted via electronic means, preferably wirelessly, to a receiver, for example a paging system, alerting appropriate medical personnel and allowing early life-saving intervention.

In accordance with another embodiment, false positive and false negative alarms can be reduced. By analyzing a greater amount of data, whether it be a continuous amount of data, multiple sources of data, multiple trends, or multiple variables, a more accurate determination of a deleterious condition can be determined. Thus, this results in fewer false positive and false negative alarms being generated reducing the risk of medical personnel becoming weary or even worse, jaded from incessant alarm conditions.

In accordance with still another embodiment of the invention, devices delivering infusions of medicine, such as narcotics, can be turned off immediately upon detection of an alarm. Similarly, other devices connected to the patient could also be turned off immediately upon detection of an alarm. In the situation where a narcotic was being administered, for example, a detection of an excessive amount of carbon dioxide in the blood could trigger the immediate and automatic cessation of the narcotic. This would allow hospital personnel to respond to the alarm to determine if the alarm was accurate and also allow remedial action to be taken while the hospital personnel are in transit to the patient's room. Remedial action could include the automatic administration of a substance to increase respiration.

Thus, the monitoring system can be used to predict a variety of conditions. It may be used to determine a deterioration of a respiratory function. It may be used to predict a proximate respiratory event, such as a respiratory arrest. It may also be used to predict opioid induced respiratory depression. It may be used to turn off the administration of such opioids. And, it may be used to control the administration of substances that increase respiration. Finally, it can be used to signal life safety personnel.

The monitoring can take place in a variety of settings. For example, it can take place in a surgical setting, a non-surgical setting, or ambulatory care setting. It can also be used in a setting where opioids are administered. For example, it can be used by dentists who administer opioids during dental procedures.

Referring now to FIG. 1, a system 100 in accordance with one embodiment of the invention can be seen. FIG. 1 shows a patient coupled with an optical probe "A". The optical probe is inserted via an IV catheter into the patient's peripheral venous system. The probe utilizes an LED, or equivalent light source, for measuring at least one or more blood analytes simultaneously, such as pH, pO2, pCO2, or temperature. A signal can be transmitted from the probe to a computer, such as computer 104. Computer 104 can then utilize the signal in a variety of ways.

For example, computer 104 can perform trend analysis of the signal to determine the accumulation of carbon dioxide in the respiratory system. Similarly, computer 104 can utilize additional measurements. For example, measurements can be taken from other locations on the patient's body, such as the umbilical artery, central venous system, peripheral arterial system, or tissue beds such as the brain, as shown by the probes labeled "D", "B", "C" and "E," respectively. Those measurements can be compared against one another as desired.

Similarly, measurement of different blood analytes and biological indicators can be used in conjunction with one another. For example, pulse oximetry measurements can be used in conjunction with measurement of carbon dioxide levels and EKG values. Thus, in some situations, one can check two or more different analyte values in conjunction with other biologic measurements for indications of the accumulation of carbon dioxide prior to signaling an alarm or implementing remedial measures. In one embodiment, those two or more analyte values can be compared against pre-determined ranges for each analyte value. Similarly, one can use the EKG device 120 or other patient monitoring devices, such as a pulse oximeter, to further detect dangerous conditions. FIG. 1 shows that computer 104 can be coupled with a memory device, such as a database 108. The database can store trended data for analysis. A medicine dispenser 112 is shown coupled with the computer. The medicine dispenser can dispense narcotics, for example. When an alarm situation is detected, the medicine dispenser can be controlled so as to inhibit the administration of the medicine. An alarm 116 is also shown coupled with the computer. The alarm can be any alarm that signals medical personnel to respond to the patient' condition. For example, it can be a wireless alarm device, e.g. a pager, carried by hospital personnel.

The computer used in system 100 can be a microprocessor based device. Furthermore, the computer can be sized so as to allow for portability and use in locations remote from a hospital, such as by paramedics or flight-for-life personnel.

Figure 2:
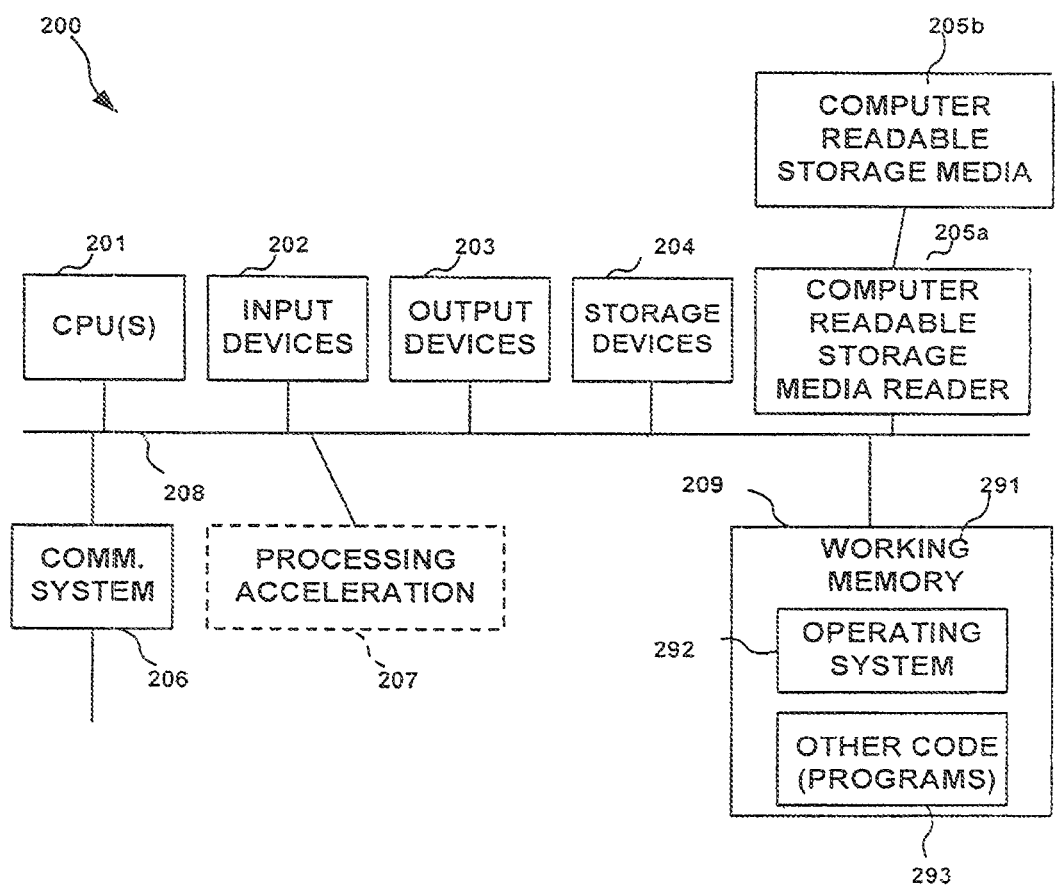
FIG. 2 illustrates a block diagram of a computing device that can be utilized as the computer shown in FIG. 1, in accordance with one embodiment of the invention.

FIG. 2 illustrates an embodiment of a computer device that could be utilized to implement the computerized device shown in FIG. 1, in accordance with one embodiment of the invention. System 200 is shown comprised of hardware elements that are electrically coupled via bus 208, including a processor 201, input device 202, output device 203, storage device 204, computer-readable storage media reader 205a, communications system 206 processing acceleration (e.g., DSP or special-purpose processors) 207 and memory 209. Computer-readable storage media reader 205a is further coupled to computer-readable storage media 205b, the combination comprehensively representing remote, local, fixed and/or removable storage devices plus storage media, memory, etc. for temporarily and/or more permanently containing computer-readable information, which can include storage device 204, memory 209 and/or any other such accessible system 200 resource. System 200 also comprises software elements (shown as being currently located within working memory 291) including an operating system 292 and other code 293, such as programs, applets, data and the like.

System 200 has extensive flexibility and configurability. Thus, for example, a single architecture might be utilized to implement one or more servers that can be further configured in accordance with currently desirable protocols, protocol variations, extensions, etc. However, it will be apparent to those skilled in the art that embodiments may well be utilized in accordance with more specific application requirements. For example, one or more system elements might be implemented as sub-elements within a system 200 component (e.g. within communications system 206). Customized hardware might also be utilized and/or particular elements might be implemented in hardware, software (including so-called "portable software," such as applets) or both. Further, while connection to other computing devices such as network input/output devices (not shown) may be employed, it is to be understood that wired, wireless, modem and/or other connection or connections to other computing devices might also be utilized.

Figure 7:
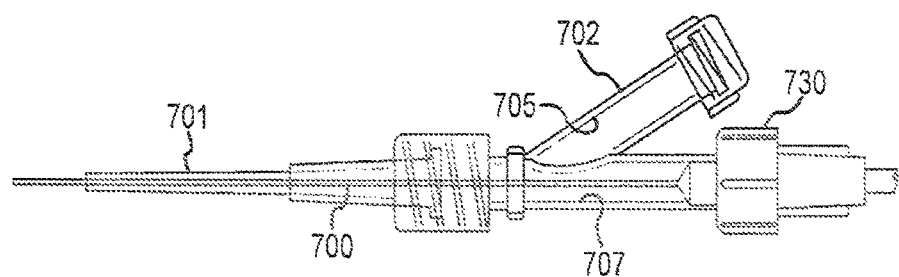
FIG. 7 illustrates an optical probe inserted via a catheter in accordance with one embodiment of the invention.
Figure 8:
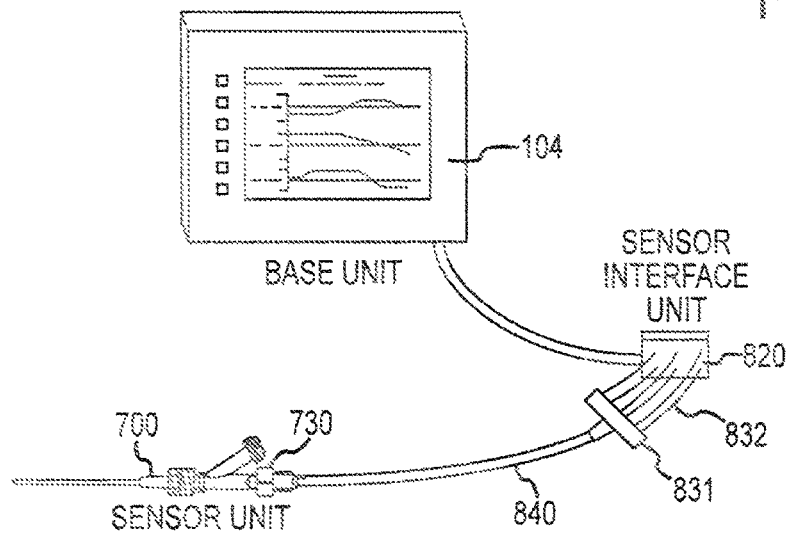
FIG. 8 illustrates a computerized monitoring of an optical probe inserted into the circulatory system of a patient in accordance with one embodiment of the invention.

One embodiment of the invention can utilize optical probes such as those described in U.S. Pat. Nos. 5,335,305; 5,397,411; and/or 5,408,999. FIGS. 7 and 8 illustrate how such probes might be used in accordance with one embodiment of the invention. Namely, FIGS. 7 and 8 show a probe 700 that has been disposed in an intra-venous cannula 701. The cannula 701 is suitable for introduction into and disposition within a human blood vessel. A tip of the probe maybe disposed in the cannula (e.g. when the cannula resides in a vein) by connecting the luer y connector 702 to the cannula and then inserting the probe 100 into the cannula through one channel 707 of the luer y connector. Whatever fluid is being introduced into or withdrawn from the cannula may be introduced or withdrawn from channel 705 of the luer y connector through which the probe 700 does not extend.

As shown in FIGS. 7 and 8, the probe 700 may then be connected to a sensor interface unit 820 (shown as separate from a base unit but which could be incorporated therein) which is connected to a base unit 104 (also shown as computer 104 in FIG. 1). The sensor interface unit provides light input to the probe and detects and measures light coming out of the probe. Signals from the unit 820 are then fed into the base unit where they are processed for display, recordation, or monitoring—especially for determining the deterioration of respiratory function.

Probe 700 may have a bundle of optical fibers 832 which extend through connector 730. The probe's bundle of fibers may be glued into a male luer with adhesive. The connector 730 is made preferably from poly carbonate plastic. The tube 840 is made preferably from polyethylene and extends from the connector 730 to a junction box 831.

Figure 3:
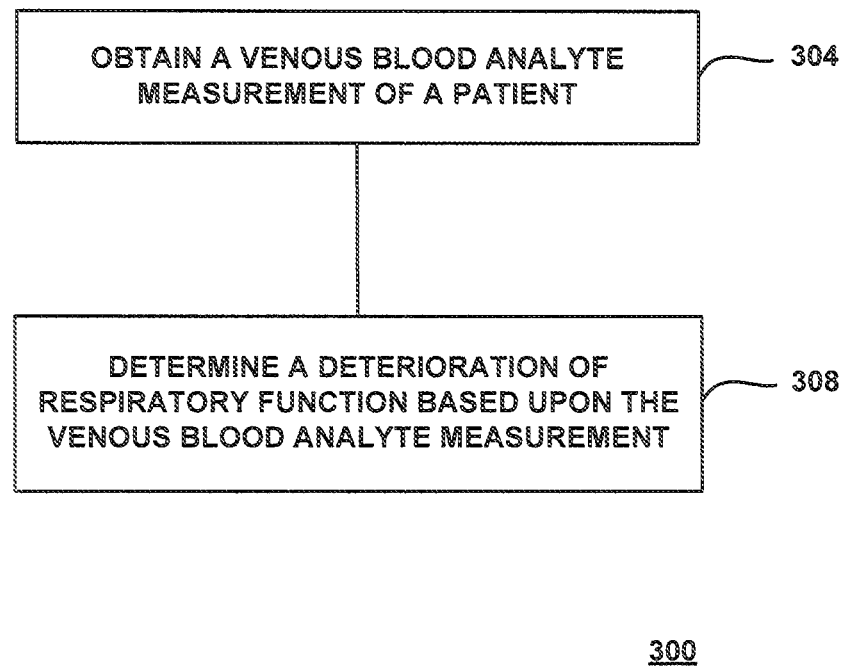
FIG. 3 illustrates a flow chart demonstrating a method of determining a deterioration of respiratory function in accordance with one embodiment of the invention.

Referring now to FIGS. 3-6, various embodiments are illustrated. FIG. 3 shows a high level flow chart 300 that illustrates a method of determining a deterioration in respiratory function. In block 304, a blood analyte measurement is taken from the patient. As explained above, the measurement is preferably taken from the venous system of the patient. In block 308, the blood analyte measurement can be used to determine if a deterioration of respiratory function is occurring or has already occurred.

Figure 4A:
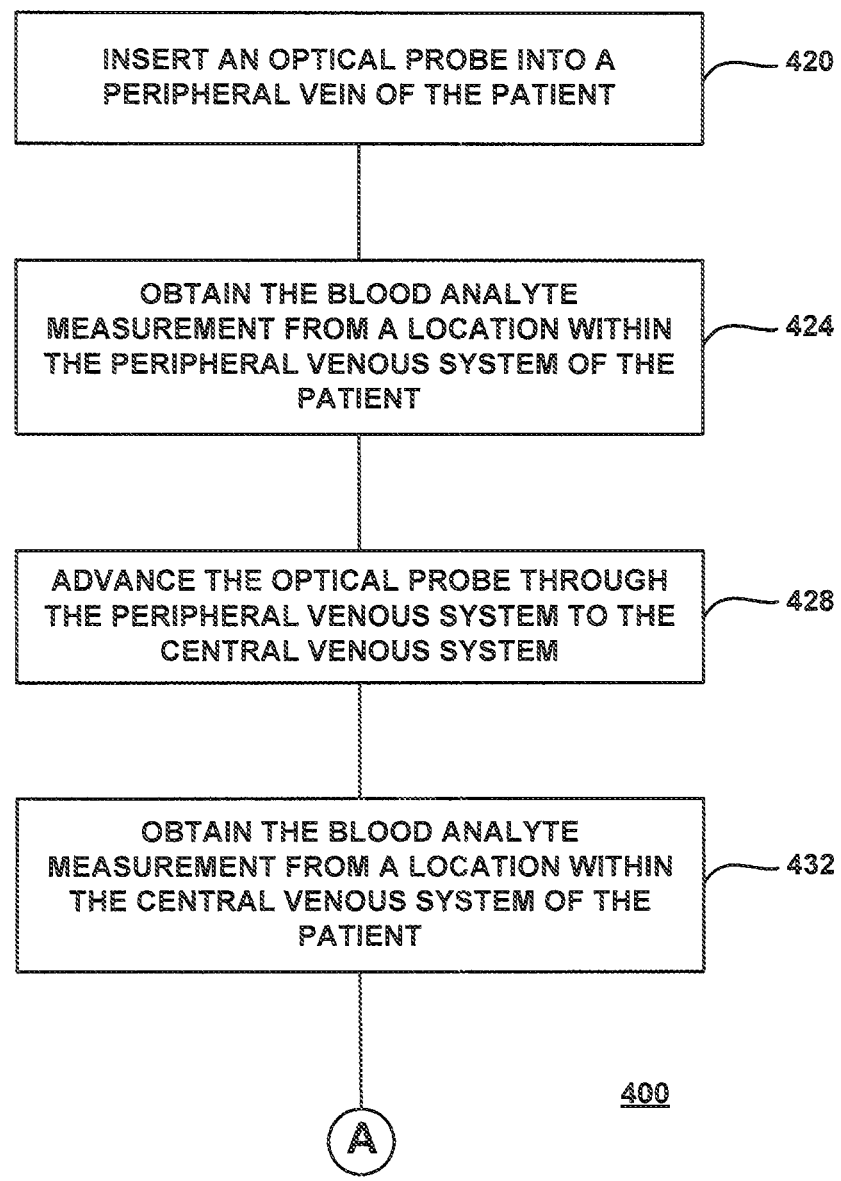
FIGS. 4A, 4B, and 4C illustrate a flow chart demonstrating a method of determining a deterioration of respiratory function in accordance with one embodiment of the invention.
Figure 4B:
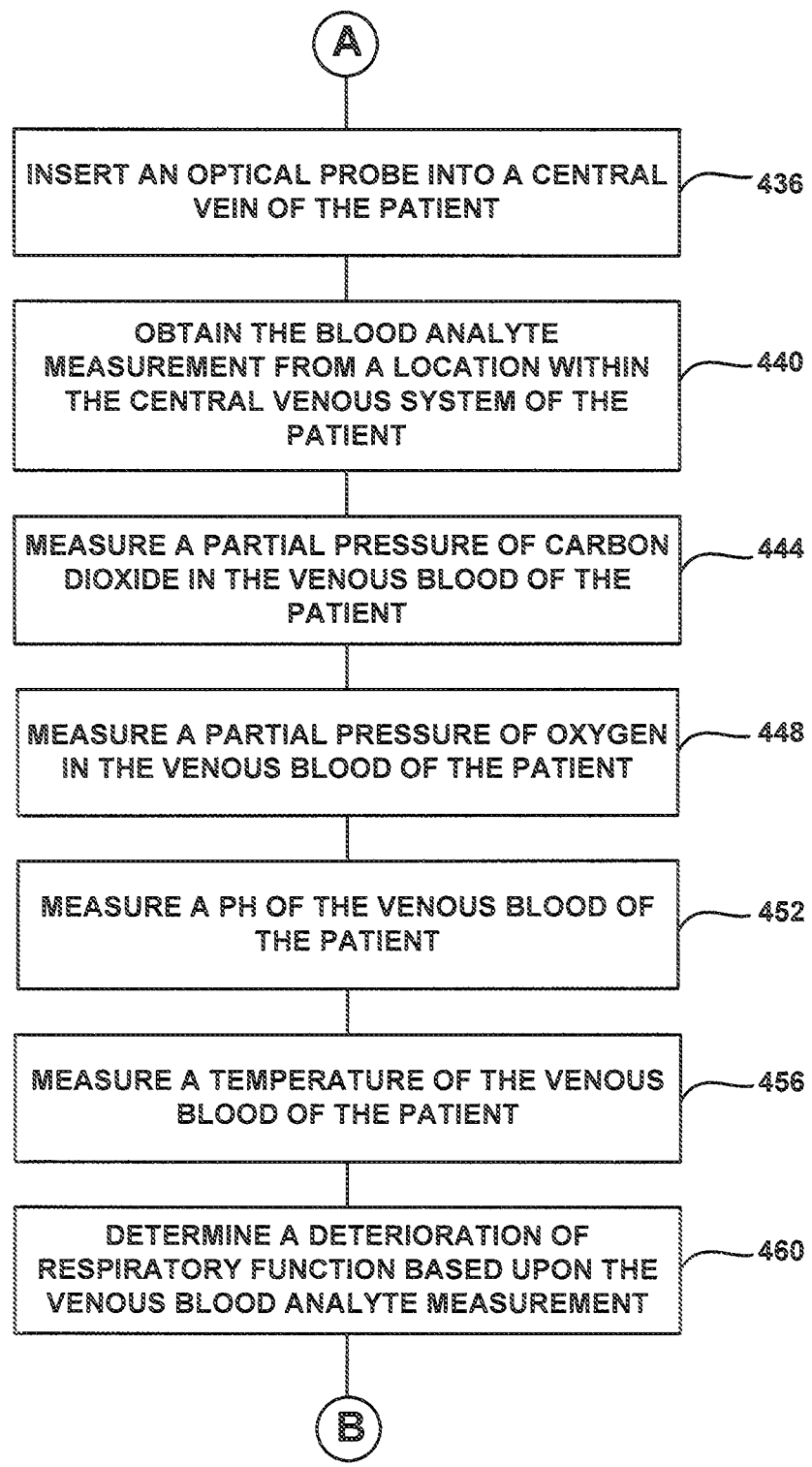
Figure 4C:
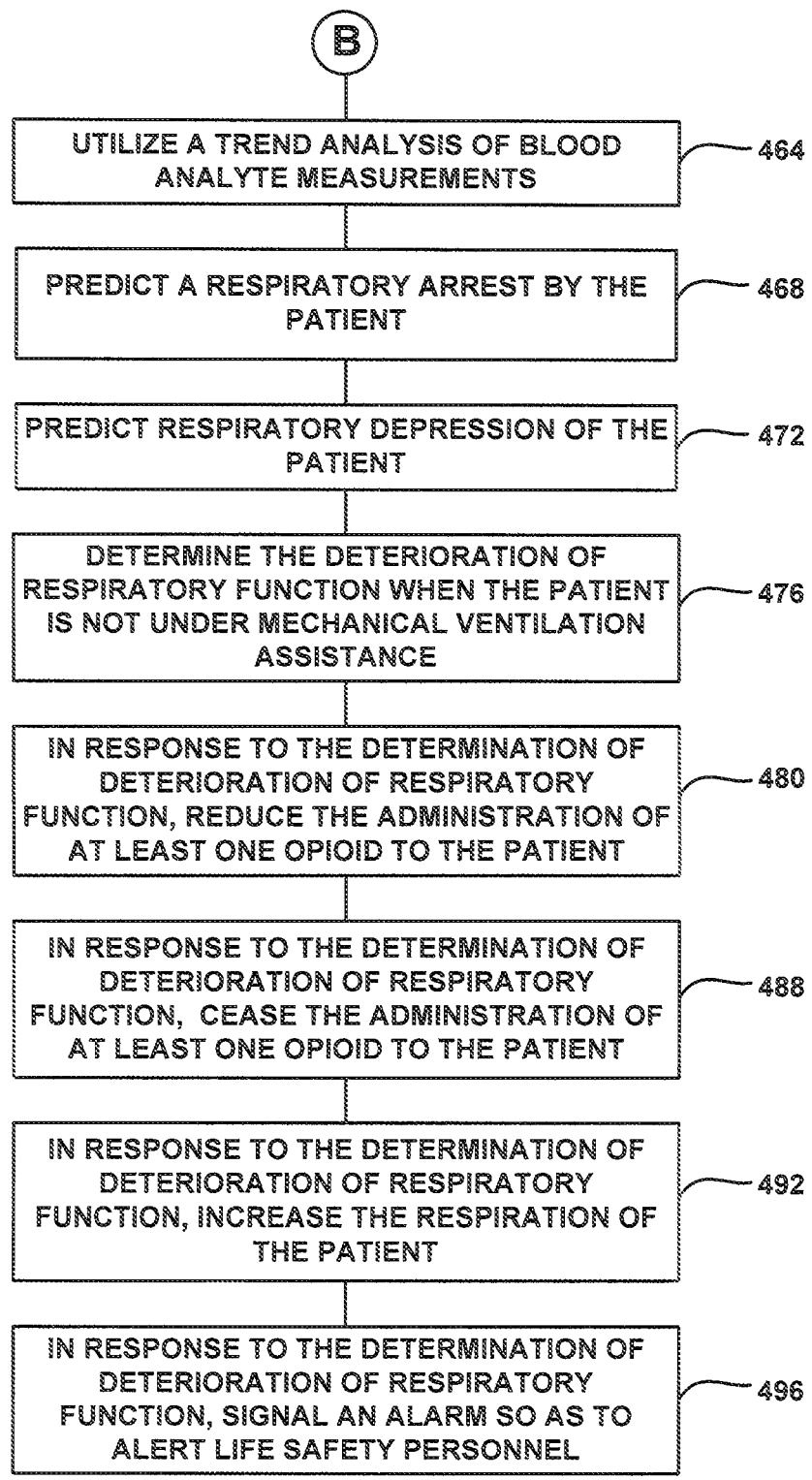

A more detailed flow chart 400 can be seen in FIGS. 4A, 4B, and 4C which illustrates a more detailed embodiment for taking and analyzing blood analyte measurements. A venous blood measurement can be taken in a variety of care settings. By way of example only, the measurements can be taken in a non-surgical setting, a surgical setting, or an ambulatory care setting. The method could be practiced in other settings as well.

To obtain a measurement, an optical probe is one type of transducer that can be used. Such an optical probe can be coupled to the patient in a variety of ways. For example, an optical probe can be inserted via a catheter in a peripheral vein of a patient, as shown by block 420. Such a catheter is often present on individuals admitted to a hospital. Thus, it provides an easily accessible access point. The probe can be positioned within the patient's circulatory system in a variety of locations. For example, block 424 shows that the probe can be positioned within the patient's peripheral venous system, such as within a vein in the patient's forearm. The probe might also be advanced through the patient's peripheral venous system to the patient's central venous system, as shown by block 428. This would allow a peripherally inserted probe to obtain a measurement from the central venous system, such as from the patient's subclavian vein, as shown by block 432. Alternatively, or additionally, a probe could be inserted into a central vein of a patient, as shown by block 436. In such an instance, a measurement could be obtained from the central venous system, as shown by block 440.

Once the transducer (such as an optical probe) is coupled to the patient, a measurement of a blood analyte can be taken. Block 444 shows that the partial pressure of carbon dioxide in the blood of the patient can be measured. Similarly, block 448 shows that the partial pressure of oxygen in the patient's blood can be measured. And, blocks 452 and 456 illustrate that the pH and temperature of the blood of the patient can be measured, respectively. In accordance with one embodiment, these measurements are preferably taken on the venous side of the patient's circulatory system.

The patient's condition may be monitored so as to evaluate his/her condition. In block 460, a determination of a deterioration of respiratory function can be made based upon the blood analyte measurement. Block 464 shows that trend analysis(ses) can be used based upon the blood analyte measurements. For example, the measurement(s) can be used to predict if the patient is approaching a respiratory arrest, as shown by block 468. Or, the measurement(s) can be used to determine if the patient is approaching respiratory depression, such as opioid induced respiratory depression, as shown by block 472.

It should be noted that block 476 highlights that this method can be performed on patients that are not under mechanical ventilation assistance. Thus, the early detection of a deterioration of respiratory function can be important for patients in such a situation as there is no on-going ventilation assistance coupled to the patient that could assist the patient prior to detecting the patient's condition.

In response to the determination that the patient's respiratory function has deteriorated, a variety of measures could be implemented. For example, block 480 illustrates that the administration of at least one opioid to the patient could be reduced and block 488 illustrates the administration of at least one opioid to the patient could be ceased. Alternatively, proactive measures could be taken to increase the respiration of the patient, as shown by block 492. This could include the administration of a medicine to cause the patient's system to respire more frequently. Or, it could involve the administration of more oxygen to the patient. Block 496 also illustrates that life safety personnel could be contacted via signaling an alarm—such as transmitting an electrical signal to an alarm system.

Figure 5:
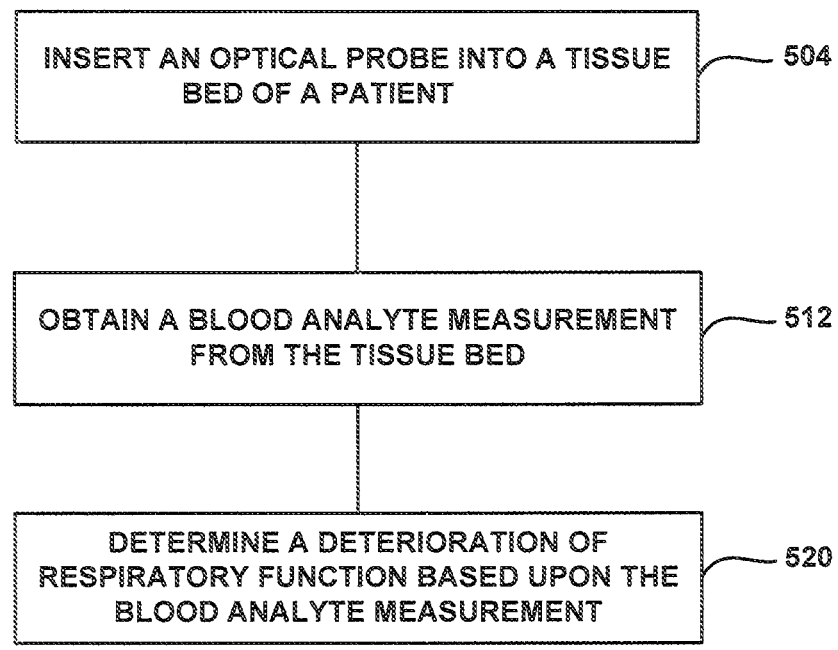
FIG. 5 illustrates a flow chart demonstrating a method of determining a deterioration of respiratory function by measuring a blood analyte from a tissue bed of a patient, in accordance with one embodiment of the invention.

In accordance with one embodiment of the invention, blood analyte measurement can be determined in ways other than inserting a transducer into a vein or artery of a patient. For example, flow chart 500 in FIG. 5 shows that a measurement can be obtained by utilizing a tissue bed of the patient. The tissue bed can be an organ, a muscle, or interstitial fluid of the patient. A transducer, such as an optical probe, can be inserted into the tissue bed as shown by block 504. Once in place, the probe can obtain a blood analyte measurement from the tissue bed, as shown by block 512. From the blood analyte measurement, a determination can be made as to whether there is a deterioration in respiratory function of the patient.

Figure 6:
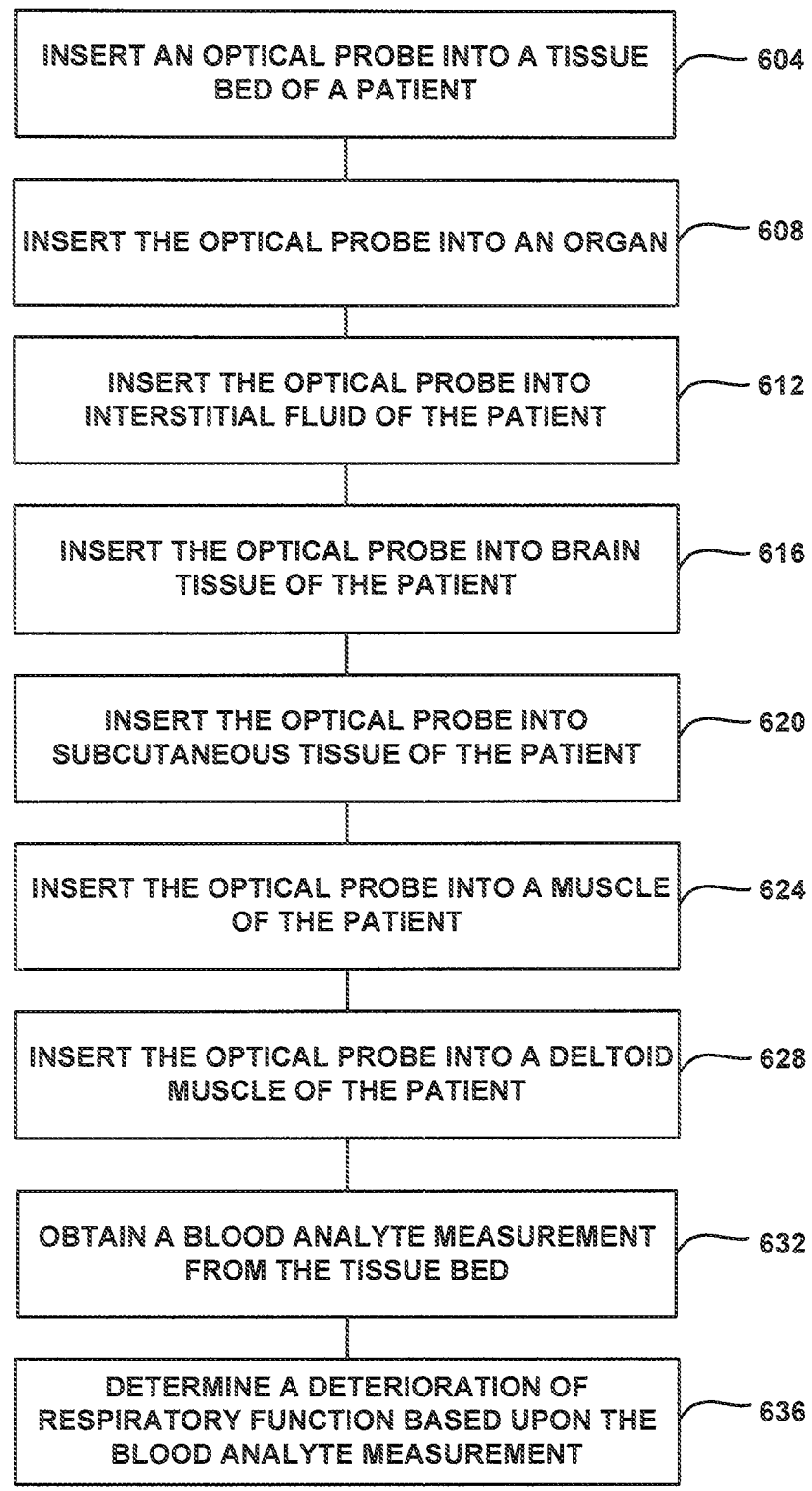
FIG. 6 illustrates a flow chart demonstrating a method of determining a deterioration of respiratory function by measuring a blood analyte from a tissue bed of a patient, in accordance with one embodiment of the invention.

FIG. 6 illustrates a more detailed flow chart 600 in accordance with one embodiment. In block 604, a transducer, such as an optical probe, is inserted into a tissue bed of a patient. The optical probe can be inserted for example into an organ, interstitial fluid, brain tissue, subcutaneous tissue, or muscle, as illustrated by blocks 608, 612, 616, 620, and 624 respectively. One possible choice for muscle insertion is a deltoid muscle of the patient, as shown by block 628.

Once the probe is inserted into the tissue bed, a blood analyte measurement can be taken, as shown by block 632. Then, a determination can be made as to whether there is or has been a deterioration of respiratory function of the patient based upon the blood analyte measurement.

While the illustrative embodiment used above has referred to a human patient, it should be noted that the systems and methods described herein could also be applied to non-human patients, as well. Thus, the use for veterinary medicine is also applicable. Also this system may be used to monitor experimentally created milieus in a research format, whether living or non-living.

While various embodiments of the invention have been described as methods or apparatus for implementing the invention, it should be understood that the invention can be implemented through code coupled to a computer, e.g., code resident on a computer or accessible by the computer. For example, software and databases could be utilized to implement many of the methods discussed above. Thus, in addition to embodiments where the invention is accomplished by hardware, it is also noted that these embodiments can be accomplished through the use of an article of manufacture comprised of a computer usable medium having a computer readable program code embodied therein, which causes the enablement of the function disclosed in this description. Therefore, it is desired that embodiments of the invention also be considered protected by this patent in their program code means as well. Furthermore, the embodiments of the invention may be embodied as code stored in a computer-readable memory of virtually any kind including, without limitation, RAM, ROM, magnetic media, optical media, or magneto-optical media. Even more generally, the embodiments of the invention could be implemented in software, or in hardware, or any combination thereof including, but not limited to, software running on a general purpose processor, microcode, PLAs, or ASICs.

It is also envisioned that embodiments of the invention could be accomplished as computer signals embodied in a carrier wave, as well as signals (e.g., electrical and optical) propagated through a transmission medium. Thus, the various information discussed above could be formatted in a structure, such as a data structure, and transmitted as an electrical signal through a transmission medium or stored on a computer readable medium.

It is also noted that many of the structures, materials, and acts recited herein can be recited as means for performing a function or step for performing a function. Therefore, it should be understood that such language is entitled to cover all such structures, materials, or acts disclosed within this specification and their equivalents, including the matter incorporated by reference.

It is thought that the apparatuses and methods of embodiments of the present invention and its attendant advantages will be understood from this specification. While the above description is a complete description of specific embodiments of the invention, the above description should not be taken as limiting the scope of the invention as defined by the claims.

What is claimed is:

1. An apparatus comprising:
an optical fiber probe for insertion into and for use in taking one or more measurements from a venous system of a patient;
a sensor interface unit to provide light input to the optical fiber probe and to measure light coming out of the optical fiber probe, the measured light coming out of the optical fiber probe being indicative of a venous blood $CO_2$ measurement;
a processor coupled with the sensor interface unit, wherein the processor is responsive to a rule to determine a deleterious amount of $CO_2$ is developing in a respiratory system of the patient based on performance of a trend analysis on a series of venous system $CO_2$ measurements obtained by the optical fiber probe, wherein one or more of the optical fiber probe and the sensor interface unit are adapted to be introducible through a peripheral intravenous catheter and advanceable from within peripheral intravenous catheter to a central vein; and an alarm system coupled with the processor and responsive to the processor based upon the determination of the deleterious amount of $CO_2$ developing in the respiratory system of the patient.

2. An apparatus comprising:

an optical probe for insertion into and for use in taking one or more measurements from a venous system of a patient;

a sensor interface unit to provide light input to the optical probe and to detect light coming out of the optical probe, the detected light coming out of the optical probe being indicative of a venous blood $CO_2$ measurement; and a processor coupled with the sensor interface unit, wherein the processor is responsive to a rule to determine a deleterious amount of $CO_2$ in the patient based on a comparison of a venous blood $CO_2$ measurement based on the detected light coming out of the optical probe with a predetermined range for $CO_2$ in venous blood, and wherein one or more of the optical probe and the sensor interface unit are adapted to be introducible through a peripheral intravenous catheter and advanceable from within peripheral intravenous catheter to a central vein.

3. The apparatus as claimed in claim 2 wherein the detected light said sensor interface unit detects includes light coming out of the optical probe indicative of a partial pressure of carbon dioxide in venous blood of the patient.

4. The apparatus as claimed in claim 2, wherein said sensor interface unit further detects light coming out of the optical probe indicative of a particle pressure of oxygen in venous blood of the patient.

5. The apparatus as claimed in claim 2, wherein said sensor interface unit further detects light coming out of the optical probe indicative of a pH of venous blood of the patient.

6. The apparatus as claimed in claim 2, wherein said sensor interface unit further measures a temperature of in blood of the patient.

7. The apparatus as claimed in claim 2, wherein said optical probe is operable for insertion into a peripheral vein of said patient, and wherein said optical probe is operable for obtaining said venous blood $CO_2$ measurement from a location within the peripheral venous system of the patient.

8. The apparatus as claimed in claim 7 wherein said processor is coupled with a medicine dispenser operable to inhibit administration of a medicine when the processor determines the deleterious amount of $CO_2$ in the patient.

9. An apparatus comprising:

an optical fiber probe for insertion into and for use in taking one or more measurements from a venous system of a patient;

a sensor interface unit to provide light input to the optical fiber probe and to detect light coming out of the optical fiber probe, the detected light coming out of the optical probe being indicative of a venous system $CO_2$ measurement; and a processor coupled with the sensor interface unit, wherein the processor is responsive to a rule to determine a deleterious amount of $CO_2$ in the patient based on a comparison of a venous system $CO_2$ measurement based on the detected light with a predetermined range for $CO_2$ in the venous system, and wherein one or more of the optical fiber probe and the sensor interface unit are adapted to be introducible through a peripheral intravenous catheter and advanceable from within the peripheral intravenous catheter to a central vein.

10. The apparatus as claimed in claim 9, wherein said sensor interface unit further detects light coming out of the optical fiber probe indicative of oxygen in the venous system of the patient.

11. The apparatus as claimed in claim 9, wherein said sensor interface unit further detects light coming out of the optical fiber probe indicative of a pH of the venous system of the patient.

12. The apparatus as claimed in claim 2, wherein the optical probe is at least partially integral to an interior of the peripheral intravenous catheter.

13. The apparatus as claimed in claim 2, wherein the optical probe is at least partially integral to a sideport device, the sideport device adapted to be couplable with the peripheral intravenous catheter while the peripheral intravenous catheter is indwelling in the patient.

14. The apparatus as claimed in claim 2, wherein the sensor interface further comprises:

a temperature sensor configured to measure a temperature of venous blood, wherein the venous blood analyte measurement includes the venous blood $CO_2$ measurement and the predetermined range for $CO_2$ in the venous blood is based on the measured temperature.

15. The apparatus as claimed in claim 2, wherein the detected light coming out of the optical probe is further indicative of a venous blood lactic acid measurement.

16. The apparatus as claimed in claim 15, wherein the processor is operable to determine a level of anaerobic metabolism based on the venous blood lactic acid measurement.

* * * * *